United States Patent
Ho et al.

(10) Patent No.: US 8,971,978 B2
(45) Date of Patent: Mar. 3, 2015

(54) CONTACT LENS WITH INTEGRATED PULSE OXIMETER

(75) Inventors: Harvey Ho, Mountain View, CA (US); Babak Amirparviz, Mountain View, CA (US)

(73) Assignee: Google Inc., Mountain View, CA (US)

(*) Notice: Subject to any disclaimer, the term of this patent is extended or adjusted under 35 U.S.C. 154(b) by 22 days.

(21) Appl. No.: 13/590,860

(22) Filed: Aug. 21, 2012

(65) Prior Publication Data
US 2014/0194708 A1    Jul. 10, 2014

(51) Int. Cl.
  *A61B 5/1455* (2006.01)
  *A61B 5/02* (2006.01)
(52) U.S. Cl.
  USPC ........... 600/318; 600/323; 600/340; 600/344; 600/500
(58) Field of Classification Search
  USPC .................. 600/318, 323, 340, 324, 500
  See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,309,085 A | 1/1982 | Morrison | |
| 4,401,371 A | 8/1983 | Neefe | |
| 4,485,820 A * | 12/1984 | Flower | 600/320 |
| 5,190,038 A | 3/1993 | Polson et al. | |
| 5,472,436 A | 12/1995 | Fremstad | |
| 5,682,210 A | 10/1997 | Weirich | |
| 5,954,644 A * | 9/1999 | Dettling et al. | 600/322 |
| 6,087,941 A | 7/2000 | Ferraz | |
| 6,131,580 A | 10/2000 | Ratner et al. | |
| 6,312,393 B1 * | 11/2001 | Abreu | 600/558 |
| 6,450,642 B1 | 9/2002 | Jethmalani et al. | |
| 6,532,298 B1 | 3/2003 | Cambier et al. | |
| 6,570,386 B2 | 5/2003 | Goldstein | |
| 6,579,235 B1 | 6/2003 | Abita et al. | |

(Continued)

FOREIGN PATENT DOCUMENTS

| | | |
|---|---|---|
| EP | 686372 | 12/1995 |
| EP | 1061874 | 12/2000 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — Eric Winakur
(74) *Attorney, Agent, or Firm* — McDonnell Boehnen Hulbert & Berghoff LLP

(57) ABSTRACT

Apparatus, systems and methods employing a contact lens having a pulse oximetry sensor to detect information indicative of a blood oxygen content and/or pulse rate of a wearer of the contact lens, are provided. In some aspects, a contact lens includes a substrate that forms at least part of a body of the contact lens and a pulse oximetry sensor located on or within the substrate that detects information associated with at least one of blood oxygen content or a pulse rate of a wearer of the contact lens. The pulse oximetry sensor comprises one or more light emitting diodes that illuminate a blood vessel of at least one of a region of an eye or an eyelid and a detector that receives light reflected from the blood vessel and generates the information.

19 Claims, 11 Drawing Sheets

(56) References Cited

U.S. PATENT DOCUMENTS

| | | |
|---|---|---|
| 6,614,408 B1 | 9/2003 | Mann |
| 6,726,322 B2 | 4/2004 | Andino et al. |
| 6,731,962 B1 * | 5/2004 | Katarow et al. ............... 600/323 |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,137,952 B2 | 11/2006 | Leonardi et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,907,931 B2 | 3/2011 | Hartigan et al. |
| 7,926,940 B2 | 4/2011 | Blum et al. |
| 7,931,832 B2 | 4/2011 | Pugh et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 2003/0179094 A1 | 9/2003 | Abreu |
| 2004/0116794 A1 | 6/2004 | Fink et al. |
| 2007/0016074 A1 | 1/2007 | Abreu |
| 2007/0121065 A1 | 5/2007 | Cox et al. |
| 2007/0188710 A1 | 8/2007 | Hetling et al. |
| 2007/0270673 A1 * | 11/2007 | Abrams et al. ............... 600/310 |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0016704 A1 | 1/2010 | Naber et al. |
| 2010/0028559 A1 | 2/2010 | Yan et al. |
| 2010/0103368 A1 | 4/2010 | Amirparviz et al. |
| 2010/0109175 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0245444 A1 | 9/2012 | Otis et al. |
| 2013/0135578 A1 | 5/2013 | Pugh et al. |

FOREIGN PATENT DOCUMENTS

| | | |
|---|---|---|
| EP | 1617757 | 1/2006 |
| EP | 1947501 | 7/2008 |
| WO | 0116641 | 3/2001 |
| WO | 03065876 | 8/2003 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'To project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3 μW Wirelessly Powered CMOS Glucose Sensor for an Active Contact Lens," 2011 IEEE International Solid-State Circuits Conference, Session 2, Feb. 21, 2011, 3 pages.

(56) References Cited

OTHER PUBLICATIONS

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
International Searching Authority, International Search Report and Written Opinion for International Application No. PCT/US2014/023671 mailed Jun. 19, 2014, 11 pages.

\* cited by examiner

CONTACT LENS WITH INTEGRATED PULSE OXIMETER

TECHNICAL FIELD

This disclosure generally relates to measuring and reporting an individual's blood oxygen saturation and pulse via a contact lens.

BACKGROUND

In various settings it is necessary or desired to measure pulse rate or blood oxygenation of an individual. Generally, hospitals and medical care givers use finger or ear lobe pulse oximeters to obtain such readings. However, these devices are difficult to wear on a routine basis as well as during performance of physical activities.

DETAILED DESCRIPTION

Figure 1A:
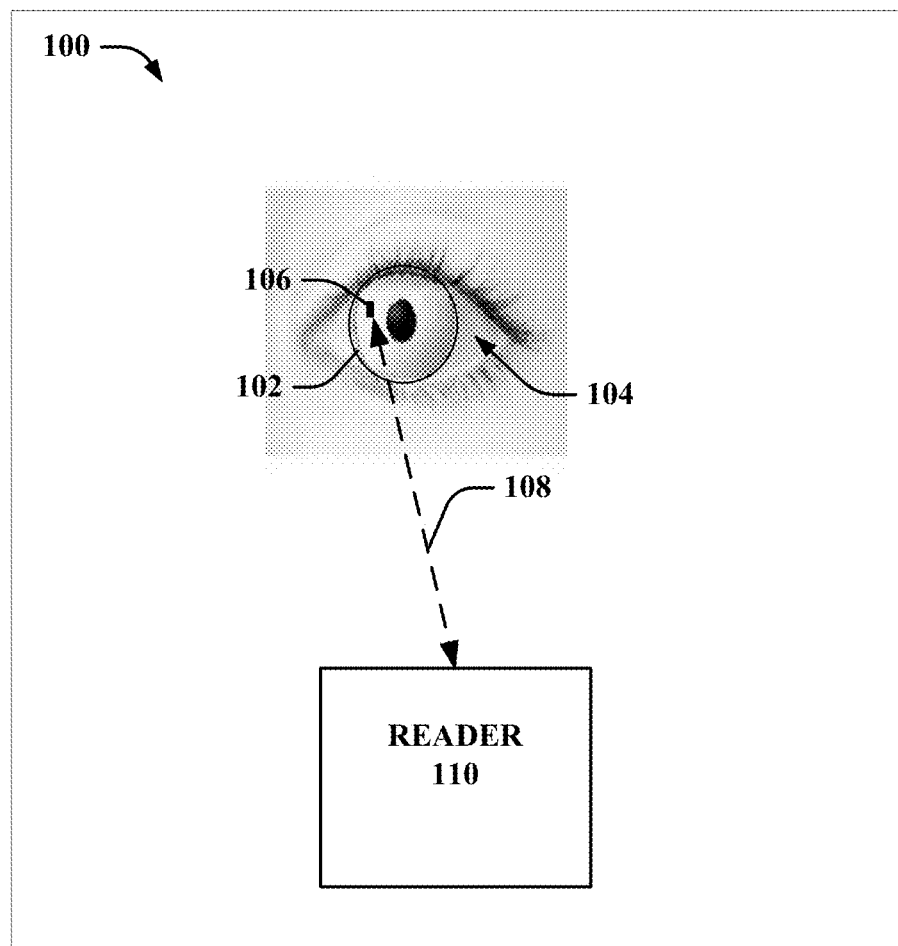
FIG. 1A is an illustration of an exemplary non-limiting system that includes a contact lens employing a pulse oximetry sensor to detect information indicative of blood oxygen content or a pulse rate of a wearer of the contact lens in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

In one or more aspects, the disclosed subject matter relates to a contact lens. The contact lens can include a substrate that forms at least part of a body of the contact lens and a pulse oximetry sensor located on or within the substrate that detects information associated with at least one of blood oxygen content or pulse rate of a wearer of the contact lens. The pulse oximetry sensor comprises one or more light emitting diodes that illuminate one or more blood vessels of at least one of a region of an eye or an eyelid, and a detector that receives light reflected from the blood vessel(s) and generates the information.

In another aspect, a method is disclosed comprising detecting information associated with at least one of blood oxygen content or pulse rate of a wearer of a contact lens using a pulse oximetry sensor located on or within the contact lens. The pulse oximetry sensor can comprise one or more light emitting diodes and a detector. In an aspect, the method comprises illuminating a blood vessel of at least one of a region of an eye or an eyelid via the one or more light emitting diodes, receiving reflected light reflected from the blood vessel at the detector, and generating the information based in part on the reflected light.

In one or more additional aspects a device is presented comprising an interface component that interfaces with and receives from a contact lens, data relating to at least one of a blood oxygen content or a pulse rate of a wearer of a contact lens, an analysis component that analyzes the received data and determines at least one of blood oxygen content or pulse rate of a wearer of a contact lens, and a display component that generates a display corresponding to the data.

The apparatus, systems, and methods disclosed herein relate to a contact lens with means for detecting and determining blood oxygen content and/or a pulse rate of a wearer of the contact lens. As used herein, the term blood oxygen content refers to percentage of hemoglobin in the blood that is saturated with oxygen (e.g. blood oxygen saturation, blood oxygenation level or $SpO_2$. The contact lens can further wirelessly transmit information pertaining to blood oxygen content or pulse rate of a wearer of a contact lens to a remote device. In an aspect, the remote device can request information from the contact lens and the contact lens can generate and transmit information in response to the request.

In order to detect an individual's blood oxygenation level and/or pulse rate via a contact lens, the contact lens can employ a pulse oximetry sensor. A pulse oximetry sensor estimates noninvasively degree of oxygen saturation of hemoglobin in arterial blood. In an aspect, the sensor of the oximeter employs one or more light sources (e.g. light emitting diodes LEDs) that radiate a section of the eye, and/or eyelid of the eye in which the contact lens is worn, with light having a known measurable signal (e.g. a known wavelength or modulated signal or known intensity of light). The light contacts hemoglobin contained in red blood cells. A certain amount of light is absorbed by the hemoglobin and a certain amount of light not absorbed and becomes reflected or transmitted. The reflected or transmitted light is sensed by a detector. The amount of light absorbed depends on the wavelength of light and level of hemoglobin oxygenation. The detector further generates a signal corresponding to the amount of light reflected or transmitted.

By knowing the wavelength of light being applied to sensor by a light source and relative amount of light being reflected/transmitted, relative blood oxygen saturation can be computed. In addition, pulse rate or the wearer of the contact lens can be determined by observing periodic changes in a signal produced by the detector. In particular, the light source can illuminate a blood vessel over a period of time as the blood vessel expands and contracts. The monitored signal bounces in time with each heart beat because arterial blood vessels expand and contract with each heartbeat. The greater amount of blood present within the blood vessel associated with each expansion affects light absorption at the detector. Similarly, the lesser amount of blood present within the blood vessel associated with each contraction affects light absorption at the detector. Therefore, by examining the varying part of the absorption spectrum, (essentially, subtracting minimum absorption from peak absorption) pulse rate of the wearer of the contact lens can be determined from the time variance between varying amounts of light detected in response to illumination of the blood vessel between blood vessel expansion and contraction.

In an aspect, signals generated by the pulse oximeter sensor of the contact lens can be captured by a local integrated circuit and analyzed by a microprocessor located on/within the contact lens itself to determine blood oxygen content and/or pulse rate of the wearer of the contact lens. The determined information can further be reported out via an RF interface. In another aspect, the detected information can be transmitted to a remote device for processing.

In an aspect, the pulse oximeter provided with the subject contact lenses can be a transmission oximeter sensor. The transmission oximeter sensor operates by transmitting light through a portion of the eye containing one or more blood vessels and measures an amount of light transmitted through the portion of the eye to a detector on an opposite side of the light source. The characteristics of light transmitted into one side of the eye can then be compared with light detected on an opposite side of the eye to compute oxygen saturation. In another aspect, the pulse oximeter provided with the subject contact lenses can be a reflectance pulse oximeter sensor. The reflectance pulse oximeter sensor measures reflected light off of a blood vessel in the eye in and/or an eyelid of the eye in which the contact lens is worn to measure blood oxygen saturation. The reflectance pulse oximetry sensor has a light source positioned on a same side of the blood vessel as the detector. In this configuration, the detector receives light that is scattered back (reflected) to the detector.

FIG. 1A is an illustration of an exemplary non-limiting system 100 that includes a contact lens 102 employing a pulse oximetry sensor to detect information indicative of blood oxygen saturation and/or pulse rate of an individual in which the contact lens 102 is worn in accordance with aspects described herein. The system 100 includes a contact lens covering at least a portion of an eye 104 and having a contact lens circuit 106. The contact lens circuit 106 can be described in greater detail with reference to FIG. 2. The contact lens circuit 106 can include the pulse oximetry sensor (not shown) to detect information indicative of blood oxygen content and/or pulse rate of the wearer of the contact lens. In particular, the pulse oximetry sensor can generate a signal corresponding to amount of light transmitted through and/or reflected off a blood vessel in the eye 104 and/or an eyelid over a period of time. The information detected by the pulse oximetry sensor can be captured via the contact lens circuit 106.

The contact lens circuit 106 including the pulse oximetry sensor can be located on and/or within a substrate of the contact lens. For example, the contact lens 102 may comprise a hydrogel substrate, such as a silicone hydrogel. One or more LEDs and/or detectors of the contact lens can further be located on and/or within a thickness of the hydrogel.

Figure 1B:
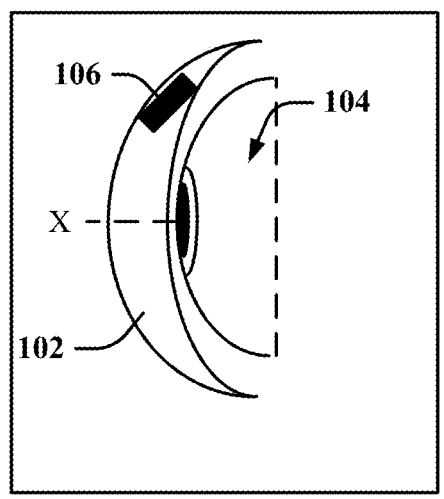
FIGS. 1B and 1C depict enlarged perspectives of an example contact lens in accordance with aspects described herein.
Figure 1C:
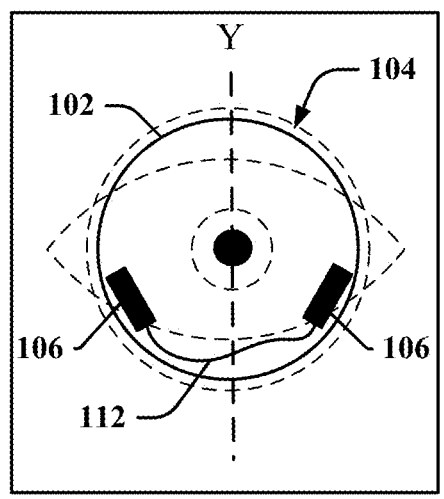

The pulse oximetry sensor can be integrated physically and/or communicatively with contact lens circuit 106. However, in some aspects, the contact lens circuit 106 may be separated physically and/or communicatively from the pulse oximetry sensor. For example, FIGS. 1B and 1C depict enlarged perspectives of an example contact lens 102 in accordance with aspects described herein. FIG. 1B depicts a cross-sectional view of contact lens 102 while FIG. 1C depicts a topical/planar view of contact lens 102.

As seen in FIG. 1B, contact lens circuit 106 is located within the substrate (e.g. within the thickness of the hydrogel) of the contact lens 102 and is depicted as a single unit. However, it should be appreciated that contact lens circuit 106 and/or one or more components associated with contact lens circuit 106 can be located on and/or within the substrate. According to this aspect, the contact lens circuit 106 and its associated components, including the pulse oximetry sensor, are co-located and communicatively coupled.

In another embodiment, as seen in FIG. 1C, one or more components of contact lens circuit 106 can be physically dispersed on and/or within the contact lens 102. For example, components of contact lens circuit 106 as presented in FIG. 1C are divided. According to this example, the pulse oximetry sensor can be physically separated from other components of the contact lens circuit. Further, components of the pulse oximetry sensor, such as one or more LEDs and/or one or more detectors can be physically dispersed on and/or within the contact lens 102 substrate. In any embodiment, one or more components of the contact lens circuit 106, including the pulse oximetry sensor, may be communicatively coupled via one or more wires 112.

Referring back to FIG. 1A, in some aspects, the contact lens 102 can include one or more components (not shown) to communicate detected and/or determined information. For example, the components can include a radio frequency (RF) antenna in some aspects. In some aspects, the information 108 can be communicated to a reader 110. In some aspects, the reader 110 can be an RF reader. Accordingly, the contact lens 102 can wirelessly communicate with a reader 110. Further, in some aspects, the reader 110 can request information from the contact lens 102 and in response, the contact lens can generate and transmit requested information.

Figure 2:
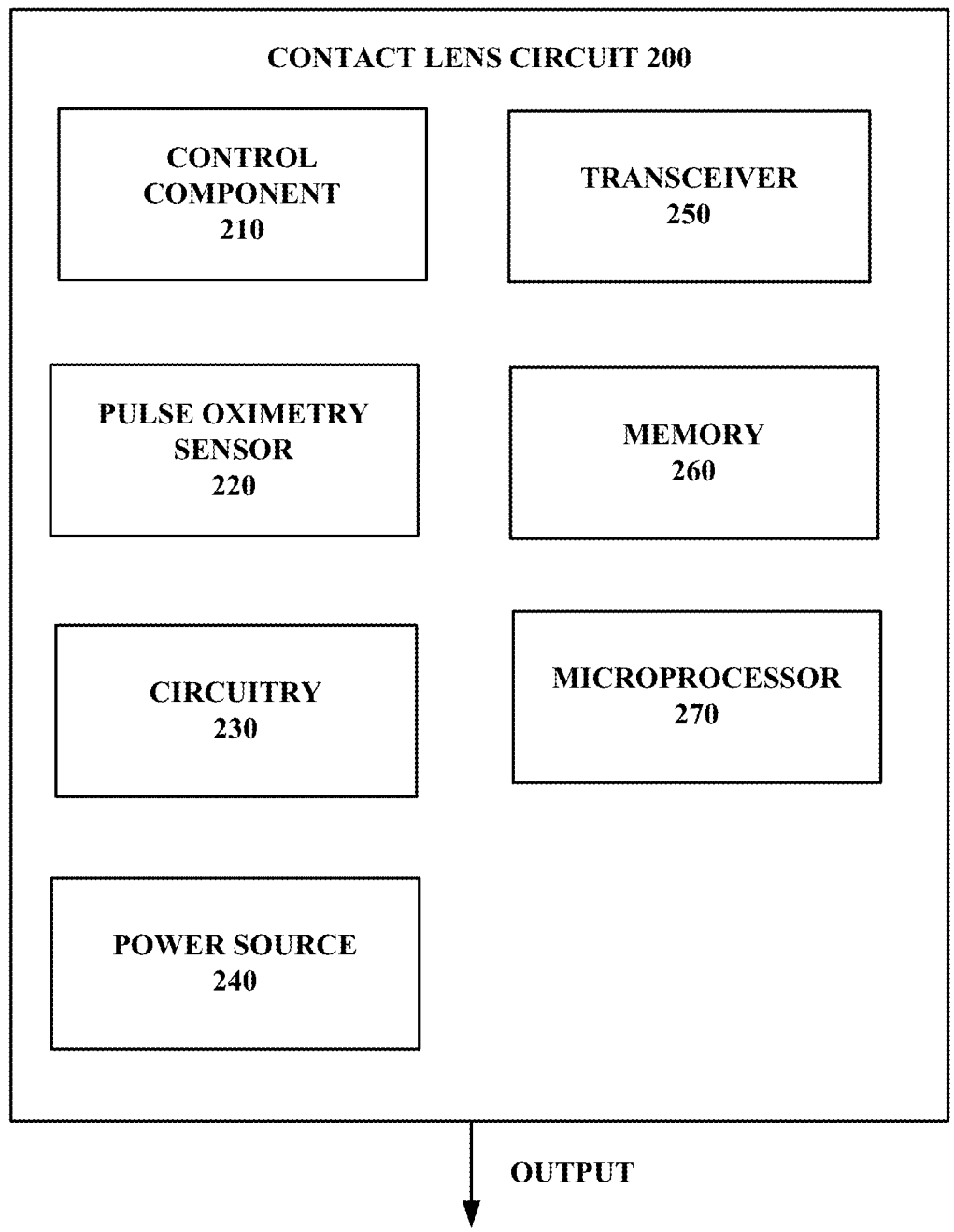
FIG. 2 is an illustration of an example contact lens circuit for a contact lens employing a pulse oximetry sensor to detect information indicative of blood oxygen content or a pulse rate of a wearer of the contact lens in accordance with aspects described herein.
Figure 3:
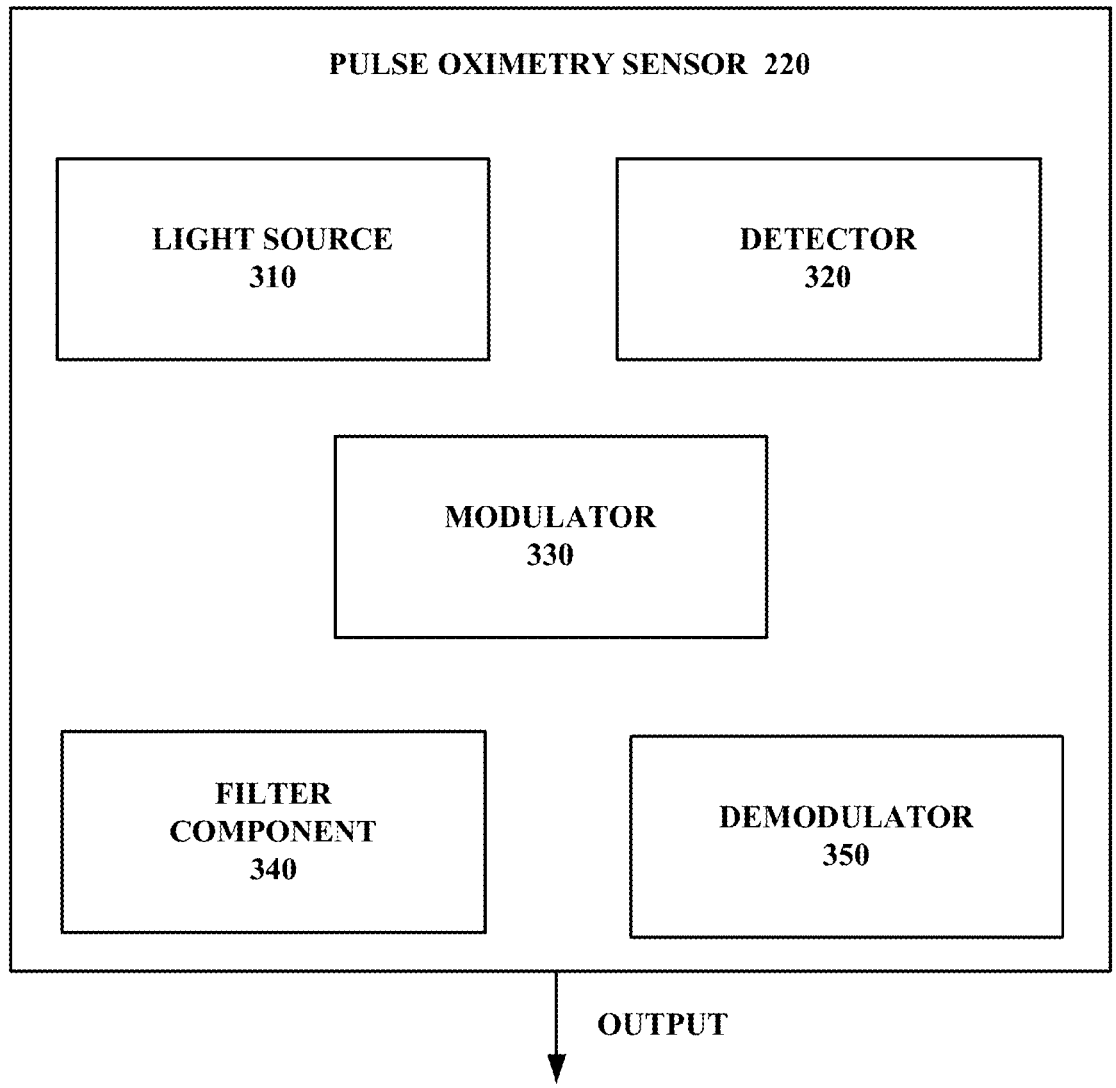
FIG. 3 is an illustration of an example pulse oximetry sensor that detects information indicative of blood oxygen content or a pulse rate of a wearer of the contact lens in accordance with aspects described herein.

FIG. 2 is an illustration of a contact lens circuit for a contact lens employing a pulse oximetry sensor in accordance with aspects described herein. FIG. 3 is a detailed depiction of a pulse oximetry sensor in accordance with aspects described herein. In various aspects, the contact lens circuit 200 can include one or more of the structure and/or functionality of the contact lens circuit 106 (and vice versa).

As shown in FIG. 2, the contact lens circuit 200 can include control component 210, pulse oximetry sensor 220, circuitry 230, power source 240, transceiver 250, memory 260 and/or microprocessor 270. In some aspects and as depicted in FIG. 2, the contact lens circuit 200 includes the pulse oximetry sensor 220 and its associated components. In other aspects, the pulse oximetry sensor 220 can be physically and/or communicatively independent (not shown) from the contact lens circuit 200. However, in any embodiment, one or more of the pulse oximetry sensor 220 and its associated components, control component 210, circuitry 230, power source 240, transceiver 250, memory 260 and/or microprocessor 270, can be operatively coupled to one another to perform one or more functions of the contact lens circuit 200.

With reference to FIG. 3, the pulse oximetry sensor 220 can include a light source 310, a detector 320, a modulator 330, a filter component 340, and/or a demodulator 350. The light source 310 can include one or more LEDs positioned on or within the substrate (e.g. hydrogel) of the contact lens. The LEDs function to illuminate a section of the eye and/or eyelid in which one or more blood vessels are located. The detector 320 collects/receives light reflected off of and/or transmitted through a blood vessel (e.g. reflected light and transmitted light). For example, in an aspect, the pulse oximetry sensor 220 can function as a reflectance pulse oximeter wherein the light source 310 and the detector 320 are on a same side as a blood vessel being illuminated by the light source 310. In another aspect, the pulse oximetry sensor 220 can function as a transmittance pulse oximeter wherein the light source 310 and the detector 320 are on opposite sides a blood vessel being illuminated by the light source 310. In response to receiving reflected and/or transmitted light, the detector 320 produces a signal corresponding to an amount of light received. In an aspect, the LEDs illuminate the blood vessel for a predetermined period of time sufficient to accurately determine a pulse rate from the signal generated by the detector. For example, the pulse oximetry sensor 220 may apply a detection interval of anywhere from about three seconds to about sixty seconds.

The amount of light received by the detector 320 depends at least in part on wavelength or known intensity of light transmitted by the light source 310 and an amount of oxygenated blood present in a blood vessel from which the received light is reflected and/or transmitted. The LEDs of the light source can transmit various types of light having various wavelengths. For example, in an aspect, the LEDs can transmit infrared light (IR). In other aspects, the LEDs can transmit visible light, including red light yellow light, green light, blue light, and purple light. Still in other aspects, the LEDs can transmit ultraviolet light (UV). Further, each of the one or more LEDs of the light source can transmit the same type of light. In another aspect, at least two of the one or more LEDs of the light source can transmit a different type of light.

In some aspects, the pulse oximetry sensor 220 can employ a modulator 330 to modulate light transmitted by the light source 310. In turn, the detector 320 can be configured to detect the modulated light signal. For example, the modulator 330 can modulate transmitted light so that the detector can better differentiate between light transmitted by light source 310 as opposed to interfering light waves from other sources (e.g. UV rays from the sun and/or ambient light). The pulse oximetry sensor (or circuit 106, circuit 200 and the like), can further employ a demodulator 350 to demodulate a received modulated signal.

In an embodiment, the light source 310 employs one or more LEDs that emit red light (R) and one or more LEDs that emit infrared light (IR). In particular, hemoglobin bound to oxygen is called oxygenated hemoglobin and has a bright red color. Hemoglobin with no oxygen bound to it is called deoxygenated hemoglobin and has a dark red color. Oxygenated hemoglobin absorbs more infrared light, while deoxygenated hemoglobin absorbs more red light. According to this embodiment, percentage of oxygenated hemoglobin (e.g. the blood oxygen saturation) and deoxygenated hemoglobin can be determined by measuring the ratio of infrared and red light received at the detector 320. In turn, oxygen saturation of blood of a wearer of the contact lens can be determined as a function of the ratio of the two waveforms in the signal generated by the detector. When amount of oxygenated hemoglobin ($HbO_2$) is greater than amount of deoxygenated hemoglobin, absorption of red light is less than absorption of infrared light, resulting in a lower ratio of absorption of the two wavelengths. In contrast, when amount of deoxygenated hemoglobin is greater than amount of oxygenated hemoglobin, absorption of red light is greater than while absorption of infrared light is less, resulting in an increased ratio of absorption of the two wavelengths.

The detector 320 converts received light into a signal representative of an amount of received. In some aspect, the signal is representative of an amount of light over a period of time. The detector 320 can include one or more detectors. In an aspect, the detector 320 can be a photodetector that comprises one or more photodiodes configured to absorb light. In some aspects, the detector 320 detects light specifically transmitted by the light source 310. According to this aspect, the detector can employ a filter component 340 comprising one or more filters that selectively filter out light not transmitted by light source 310. For example, the filter can selectively allow only a signal having a known modulation scheme to be received at the detector 320. In another aspect, as discussed in greater detail below, the detector component 320 can detect all suitable forms of light received at the detector. For example, the detector can detect environmental light (e.g. sunlight, ambient light or natural light) in addition to light transmitted by light source 310. According to this aspect, the detector 320 can employ various means to differentiate between received light forms and generate an output signal that differentiates between the received light forms. For example, the detector can differentiate between modulated and non-modulated light signals using various filters and/or demodulation schemes.

In an embodiment, the pulse oximetry sensor 220 is configured to detect information regarding an amount of light transmitted through a blood vessel by employing environmental light as a light source. According to this embodiment, eye blinks can be employed to capture environmental light levels. By using the light levels between an open eye and a closed eyelid it is possible to calculate the absolute amount of oxygen in vessels in the eyelid (e.g. via microprocessor 270 or processor 650 as discussed below).

In an aspect, the pulse oximetry sensor can operate without an internal light source 310 or with the internal light source 310 turned off. In particular, a detector 320 can be located on an area of a contact lens that is not covered by an eyelid when the eye in which the contact lens is worn is open. Therefore when the eye is open, the detector can receive environmental light. The detector 320 can further be configured to gather multiple reading of an amount of environmental light received directly (e.g. not transmitted through a blood vessel), in order to obtain an accurate measurement signal for direct environmental light. In addition, the detector 320 can be configured to measure an amount of light received when a wearer closes his or her eyelid and no internal light source 310 is employed/turned on. Such light received will be the amount of environmental light transmitted through a blood vessel in the eyelid from the environmental light.

In some aspects, readings of direct environmental light and transmitted environmental light (light transmitted through a blood vessel in the eyelid) can be employed to determine blood oxygenation levels and pulse without the need of any additional sensed/detected information by the pulse oximetry sensor. In other aspects, signals produced by the detector 320 corresponding to direct environmental light and transmitted environmental light can be employed as calibration information. Such calibration information can be employed in conjunction with additional pulse oximetry sensor 220 readings obtained using light source 310 to more accurately determine blood oxygenation levels. For example, between successive blinks, the detector 320 can recalibrate what the baseline environmental light level is and use that baseline to correlate the oxygenation level.

It should be appreciated that components of the pulse oximetry sensor 220 such as light source 310 and detector 320 can be integrated at various locations on and/or within the substrate of the contact lens. For example, LEDs can be located at multiple locations within a contact lens and orientated to emit light at different sections of the eye and/or eyelid of the eye in which the contact lens is worn. Further, one or more detectors can be positioned on or within the contact lens so that light transmitted through and/or reflected off of a blood vessel, in response to illumination by the light source or in response to illumination by environmental light, is received at the one or more detectors.

Referring back to FIG. 2, in addition to the pulse oximetry sensor, the contact lens circuit 200 can further include control component 210, circuitry 230, power source 240, transceiver 250, memory 260 and/or microprocessor 270. Control component 210 controls the operations of contact lens circuit 200, including operation of the pulse oximetry sensor 220. Circuitry 230 provides connections between components of the contact lens circuit 200 to facilitate operation of the contact lens circuit. For example circuitry 230 facilitates collection of signals generated by the pulse oximetry sensor 220. Circuitry 230 can further send detected signals/values to transceiver 250, memory 260, and/or microprocessor 270. Power source 240 can include any suitable power source that can provide necessary power for the operation of various components of the contact lens circuit 200. For example, the power source 240 can include but is not limited to a battery, a capacitor, a solar power source, or mechanically derived power source (e.g., MEMs system). Transceiver 250 transmits and receives information to and from contact lens circuit 200. In some embodiments, the transceiver 250 can include an RF antenna.

In an aspect, the control component 210 directs operation of the pulse oximetry sensor 220 according to a preconfigured protocol stored in memory 260. In other aspects, the control component 210 directs operation of the pulse oximetry sensor according to instructions received, via the transceiver 250, from an external device (e.g. reader device 110). In an aspect, the pulse oximetry sensor 220 can perform a variety of sensing mechanisms to collect information indicative of a contact lens wearer blood oxygen saturation and/or pulse. It should be appreciated that control component 210 facilitates operation of the various mechanisms of the pulse oximetry sensor. For example, in an aspect, the pulse oximetry sensor can collect data in response to illumination of its light source 310. In other aspects, the pulse oximetry sensor can collect data in response to illumination by environmental light.

In an aspect, illumination of the light source of the pulse oximetry sensor 220 is a collective on/off operation. However, in other aspects, the light source may include multiple LEDs that can be independently controlled. Still in yet another aspect, the pulse oximetry sensor may not employ a light source 310 at all and merely operate using environmental light. For example, the pulse oximetry sensor can include a first set of LEDs that emit a first type of light towards a blood vessel in an upper eyelid of the eye in which the contact lens is worn and a second set of LEDs that emit a second type of light towards a blood vessel in the eye. According to this aspect, the control component 210 can independently direct operation of the light source 310 so that different sets of LEDs are turned on and off at different times. In addition, a detector 320 of the pulse oximetry sensor 220 can detect light (e.g. direct environmental light and/or transmitted environmental light) when the light source 310 is not turned on/not employed. Accordingly, the control component 210 can further control the detecting of light signals when the light source of the pulse oximetry sensor 220 is not turned on/not employed.

In an embodiment, the control component 210 controls operation of the pulse oximetry sensor to collect direct environmental light and/or transmitted environmental light. In some aspects, readings of direct environmental light and transmitted environmental light (light transmitted through a blood vessel in the eyelid) can be employed to determine blood oxygenation levels without the need of any additional sensed/detected information by the pulse oximetry sensor. In other aspects, signals produced by the detector 320 corresponding to direct environmental light and transmitted environmental light can be employed to calibrate the pulse oximetry sensor. For example, when an individual initially places a contact lens having circuit 200 into his or her eye, the contact lens may need to be calibrated in order to produce accurate readings of the individual's blood oxygen level and/or pulse.

The control component 210 can direct the detector of pulse oximetry sensor to obtain one or more readings of direct environmental light. The multiple readings can then be averaged to obtain an accurate measurement of environmental light. In some aspect, the control component 210 can direct the pulse oximetry sensor to re-calibrate, (e.g. obtain a new measurement for direct environmental light). In order to detect transmitted environmental light, the detector 320 detects light received when an eyelid covers the detector. In some aspects, the control component 210 directs the detector to collect transmitted environmental light signals when a wearer blinks. In other aspects, a wearer of the contact lens can facilitate generation of transmitted environmental light measurements.

For example, a wearer of a contact lens can voluntarily close his or her eye for a predetermined period of time (as defined by instructions provided with the contact lens at the time of purchase or etc.). Such closing of the eye can be sensed by the detector and/or the control component and prompt the detector to perform detection of transmitted environmental light. In another example, the wearer of the contact lens can cooperate with a reader device. According to this example, the reader device can instruct a wearer of a contact lens when and for how long to close and open his or her eye in order to obtain detected light measurements when the eye is closed (e.g. transmitted environmental light measurements). The reader device can further direct, via wirelessly transmitted control signals, the pulse oximetry 220 sensor to obtain detector readings when the eye is closed and opened.

In an aspect, in order to generate information that can be employed to determine pulse or blood oxygenation, the pulse oximetry sensor can generate data when the light source 310 is operated under various configurations. For example, the control component 210 can direct the pulse oximetry sensor to generate data when the light source is turned collectively on and off, and/or when the light source is turned collectively on and off when the wearer of the contact lens completely closes his or her eye. It should be appreciated that readings requiring opening and closing of an eye can be obtained in response to involuntary blinking by a wearer or directed closing of the eye by the wearer in response to instructions provided to the wearer. As noted above, such instructions may be provided with the contact lens at purchase or by a reader device that cooperates with the contact lens.

In another example, information that can be employed to determine pulse or blood oxygenation can be measured by illuminating different sets of LEDs of the light source, where the different sets of the LEDs of the light source either illuminate different blood vessels or emit different types of light. It should be appreciated that sensor readings under various test/calibration conditions can serve as baseline information from which a wearer's actual blood oxygen level and/or pulse rate can be calculated (e.g. via microprocessor 270 and/or analysis component 530).

In an aspect, the pulse oximetry sensor 220 performs detection of information indicative of oxygen saturation and/or pulse (e.g. amount of light received at the detector of the pulse oximetry sensor and/or periodic fluctuations in the amount of light received) on a continuous basis. For example, assuming the pulse oximetry sensor 220 is calibrated or has previously generated calibration information, the pulse oximetry sensor 220 may operate at the direction of control component 210 according to a programmed schedule defined in memory 260. For example, the programmed schedule may direct detection of information indicative of oxygen saturation and/or pulse by the pulse oximetry sensor 220 every thirty seconds, every minute, every thirty minutes, every hour, and etc. For instance, the pulse oximetry sensor 220 can illuminate blood vessels in the eye and detect reflected and/or transmitted light in response to the illumination, according to a schedule. According to this aspect, transceiver 250 can further be configured to transmit detected information according to a same or similar programmed schedule as the pulse oximetry sensor 220. For example, the detected information can be transmitted to a reader device for processing thereof. However, in some aspects, the detected information is analyzed and processed at the contact lens circuit via microprocessor 270. For example, microprocessor 270 may determine or infer the blood oxygen saturation level and/or pulse of the wearer of the contact lens based on the signals generated by the pulse oximetry sensor.

In another aspect, where microprocessor 270 analyzes detected information to determine the blood oxygen saturation level and/or pulse of the wearer of the contact lens, the transceiver 250 can be configured to transmit data indicating a determined blood oxygen level and/or pulse rate when the determined data is outside of a predetermined range. For example, the pulse oximetry sensor may routinely detect information indicative of blood oxygen level and/or pulse rate or the wearer of the contact lens and the microprocessor may routinely determine the blood oxygen level and/or pulse rate based on the detected information. When the blood oxygen level and/or pulse rate falls outside a predetermined range, the transceiver 240 may send an alert to a reader device. For example, an athlete may wear a contact lens having circuit 200. As the athlete is exercising, he may desire to monitor his blood oxygen level and heart rate. In an aspect, when his heart rate and/or blood oxygen level is too high or too low, he may receive a message at a personal device, such as a cell phone or ear monitor, indicating his heart rate and/or blood oxygen level.

In yet another aspect, the pulse oximetry sensor 220 can perform detection of blood oxygen saturation and pulse rate information in response to a request signal. For example, transceiver 250 can receive a request from a remote device (e.g. a reader device 110) for information indicative of blood oxygen saturation and/or pulse rate of a wearer of the contact lens. In turn, the detection component 210 can detect the information. In some aspects, the microprocessor 270 can further determine the wearer's blood oxygen saturation and/or pulse rate based on the detected information. The transceiver 250 can then transmit the detected and/or determined information back to the reader device.

Processing of information detected by the pulse oximetry sensor 220 can be performed by a remote device processor and/or microprocessor 270. Microprocessor 270 and/or a remote processor can employ various mechanisms in order to determine blood oxygen content and/or pulse rate from information detected by the pulse oximetry sensor 220. In general, the pulse oximetry sensor 210 produces an electrical signal corresponding to an amount or magnitude of light received at the detector over the course of a period of time. In some aspects, the light received is reflected light while in other aspects, the light received is transmitted light. Blood oxygen content and/or pulse rate can be determined based at least in part on the amount/magnitude of light received at the detector and fluctuations in the amount of light received over time (in response to blood vessel expansion and contraction with each heart beat).

In addition, a variety of other factors that can influence blood oxygen saturation and/or pulse rate determinations, including but not limited to: calibration information, conditions under which the light is received (e.g. eye open/closed) type of light received at the detector (e.g. environmental light, transmitted light, reflected light, wavelength, intensity of light), position of the light source with respect to the detector, position of blood vessel illuminated by the light source, size shape and thickness of the contact lens substrate, material of the substrate, or saturation level of the substrate.

Microprocessor 270 (and/or an external processor) may employ various algorithms or look up tables that relate detected information to blood oxygen saturation levels and/or pulse rate. For example, where the light source of the sensor transmit red light and infrared light, the microprocessor can determine the percentage of oxygenated hemoglobin (e.g. the blood oxygen saturation) and deoxygenated hemoglobin in an individual's blood by calculating the ratio of infrared and red light received at the detector. The output ratio can further be correlated to a blood oxygen level using a look up table stored in memory 260.

In various embodiments, memory 260 can store information detected by the pulse oximetry sensor. Further, memory 260 can store any information necessary for microprocessor 270 (and/or an external processor) to perform calculations and determinations of a wearer's blood oxygen content and/or pulse. For example, memory 260 can store algorithms, look up tables and known values required for the algorithmic calculations that are configured to compute blood oxygenation level and/or pulse rate (e.g. calibration information, type of light employed by the light source, features of possible light signals detectable by the detector, position of the light source with respect to the detector, modulation and demodulation information, position of blood vessel illuminated by the light source, size shape and thickness of the contact lens substrate, material of the substrate, or saturation level of the substrate and etc.). Memory 260 can further store computer-executable instructions for execution by the microprocessor 270. The microprocessor 270 can execute computer-executable instructions to perform one or more functions of the contact lens circuit 200.

In an embodiment, microprocessor 270 (and/or an external processor) can employ various (explicitly or implicitly trained) classification schemes or systems (e.g., support vector machines, neural networks, expert systems, Bayesian belief networks, fuzzy logic, data fusion engines, etc.) in connection with performing analysis of detected information. A classifier can map an input attribute vector, x=(x1, x2, x3, x4, xn), to a confidence that the input belongs to a class, such as by f(x)=confidence(class). Such classification can employ a probabilistic or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Figure 4B:
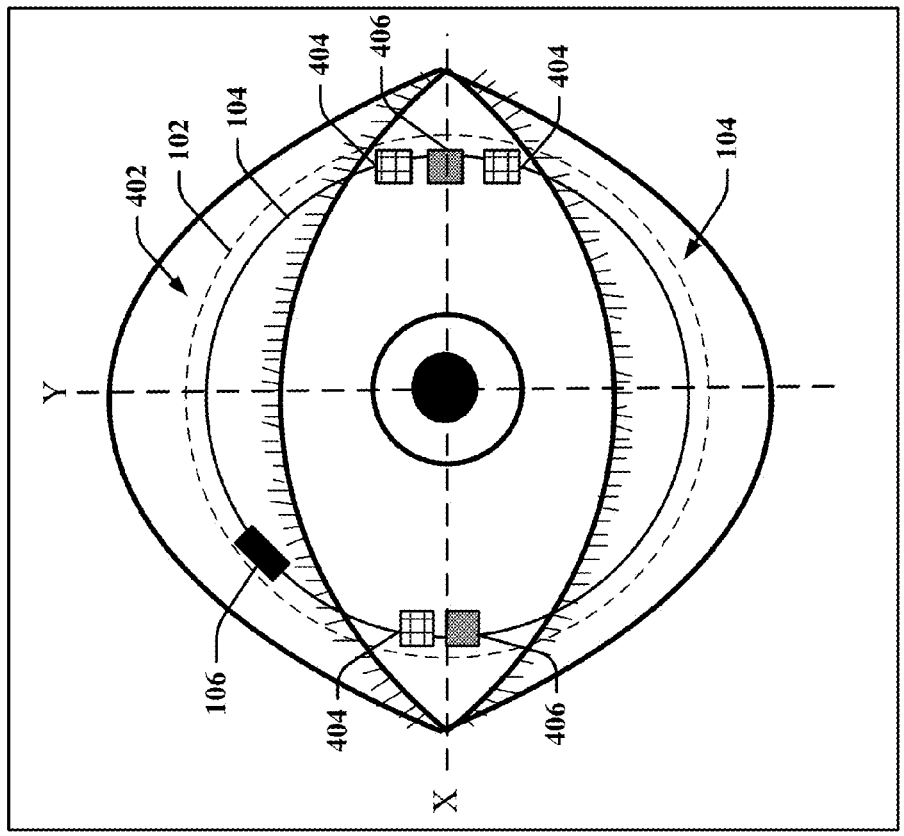
FIGS. 4A-4E depict various perspectives of an example contact lens employing a pulse oximetry sensor to detect information indicative of blood oxygen content or pulse rate of a wearer of the contact lens in accordance with aspects described herein.
Figure 4A:
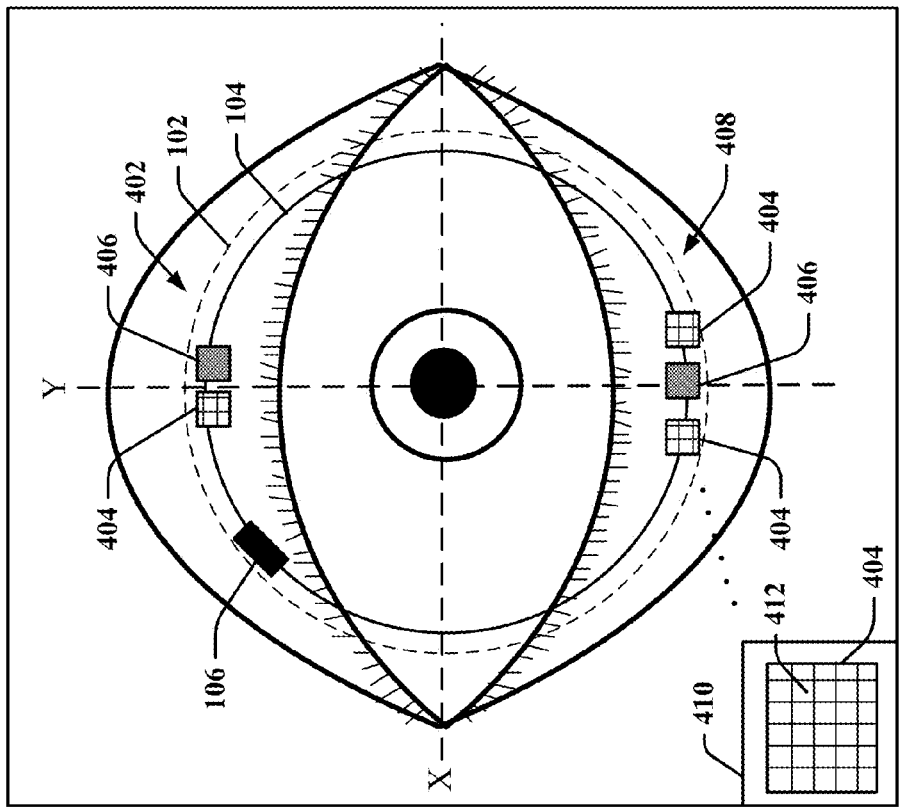
Figure 4E:
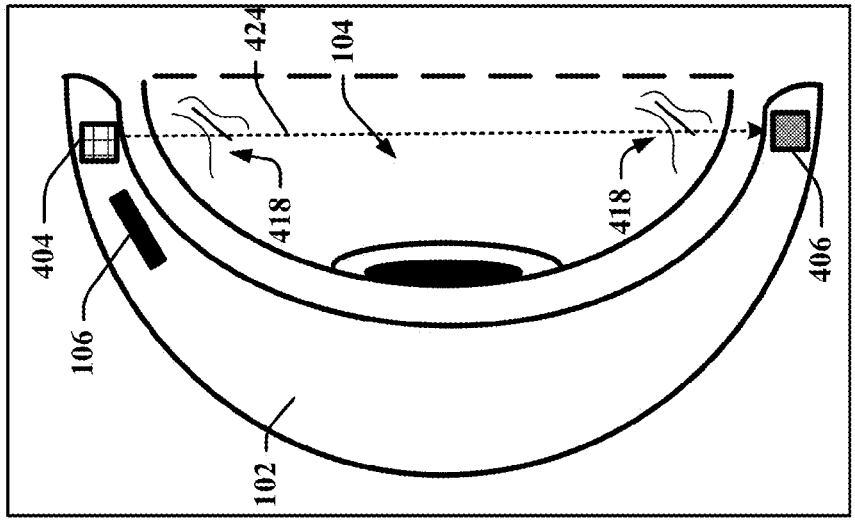
Figure 4D:
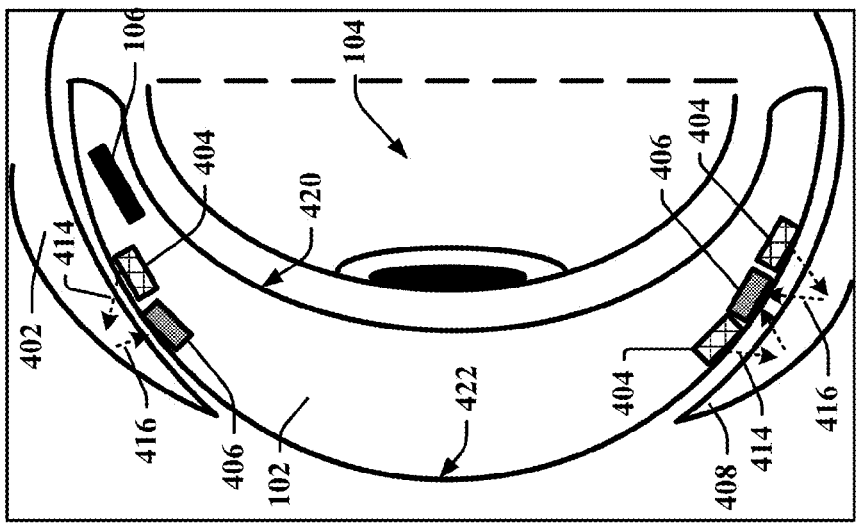
Figure 4C:
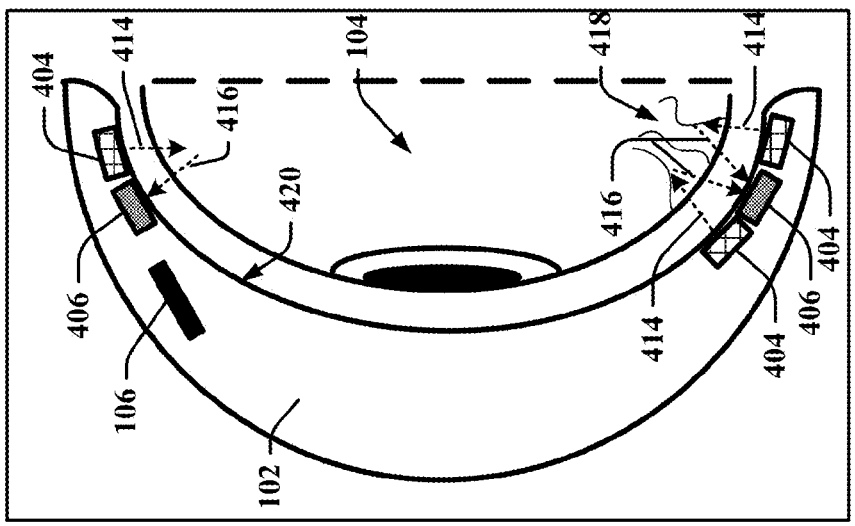

With reference now to FIGS. 4A-4E, presented are different perspectives of example contact lenses 102 employing a contact lens circuit (e.g. contact lens circuit 106, 200) having a pulse oximeter sensor (e.g. sensor 220). FIGS. 4A and 4B depict top planar views of example contact lenses and FIGS. 4C, 4D, and 4E present cross-sectional views of example contact lenses. It should be appreciated that features of the example contact lenses and the eye in which the example contact lenses are worn in FIGS. 4A-4E are not drawn to scale. Certain features are exaggerated merely for exemplary purposes. Further, it should be appreciated that although the example contact lenses 102 in FIGS. 4A-4E are depicted having multiple light sources and multiple detectors, the contact lenses are not limited to such configurations. For example, an example contact lens can have any number N of light sources and detectors. In addition, any of the light source/detector configurations of example contact lenses 102 in FIGS. 4A-4E may be combined onto a single contact lens.

Turning initially to FIG. 4A, presented is a top planar view of an example contact lens 102 (represented by the dashed line) being worn in/on an eye 104. The eye 102 depicted in FIG. 4A is considered open. The eye 104 is depicted having an upper eyelid 402 and a lower eyelid 408 which cover at least part of the contact lens when the lens 102 is worn in the eye and the eye is open. The contact lens 102 includes a contact lens circuit 106 and a pulse oximetry sensor consisting of multiple light sources 404 and detectors 406. One or more wires (not shown) can connect the contact lens circuit 106, light sources 404 and/or detectors 406. It should be appreciated that the multiple light sources and detectors of contact lens 102 are merely presented to demonstrate different configurations of light source and detector locations. In some aspects, one or more light sources and/or detectors can be removed and/or rearranged on the contact lens 102.

As seen in FIG. 4A, in an aspect, a light source 404 and a detector 406 can be located side by side on the contact lens 102 in a area that is covered by the upper eyelid 402 when the eye is open (e.g. on or around axis Y). According to this aspect, the light source 404 may emit light towards a blood vessel in the upper eyelid 402 and the detector 406 may receive light reflected from the blood vessel. In another aspect, the light source 404 may emit light towards a blood vessel in the portion of the eye covered by the upper eyelid 402 and the detector 406 may receive light reflected from the blood vessel. Similarly, in an aspect, the contact lens 102 may have two light sources located on either sides of a single detector 404, a shown in the area covered by the lower eyelid 408. The two light sources 404 in the area below the lower eyelid 408 may also emit light towards a blood vessel in the eye 104 or the lower eyelid 408, and the light reflected off of the blood vessel can be received at the detector 406 located there between. In an aspect, by locating the light sources 404 and the detectors in areas covered by an eyelid even when the eye is open, external interfering light signals can be reduced.

In an aspect, a light source 404 can consist of a single LED. In another aspect, a light source can consist of two or more LEDs. For example, box 410 presents an enlarged picture of a light source 404. As seen in box 410, light source 404 comprises an array of LEDs 412. In particular, the light source 404 in box 410 comprises thirty LEDs by way of example.

Turning now to FIG. 4B, presented is another top planar view of an example contact lens 102 (represented by the dashed line) being worn in/on an eye 104. The eye 102 depicted in FIG. 4B is considered open. The eye 104 is depicted having an upper eyelid 402 and a lower eyelid 408 which cover at least part of the contact lens when the lens 102 is worn in the eye and the eye is open. The contact lens 102 includes a contact lens circuit 106 and a pulse oximetry sensor consisting of multiple light sources 404 and detectors 406. One or more wires (not shown) can connect the contact lens circuit 106, light sources 404 and/or detectors 406. It should be appreciated that the multiple light sources and detectors of contact lens 102 are merely presented to demonstrate different configurations of light source and detector locations. In some aspects, one or more light sources and/or detectors can be removed and/or rearranged on the contact lens 102.

As seen in FIG. 4B, in an aspect, one or more light sources 404 can be located aside a detector 406 on the contact lens 102 in a area that is not covered by an eyelid 402 when the eye is open (e.g. on or around axis X). According to this aspect, the light source(s) 404 may emit light towards a blood vessel in the portion of the eye that is not covered by an eyelid 402 or 408 and the detector 406 can receive light reflected from the blood vessel.

Continuing to FIG. 4C, presented is a cross-sectional view of an example contact lens 102 being worn in/on an eye 104. The eye 102 depicted in FIG. 4C is considered open. The contact lens 102 includes a contact lens circuit 106 and a pulse oximetry sensor consisting of multiple light sources 404 and detectors 406. One or more wires (not shown) can connect the contact lens circuit 106, light sources 404 and/or detectors 406. It should be appreciated that the multiple light sources and detectors of contact lens 102 are merely presented to demonstrate different configurations of light source and detector locations. In some aspects, one or more light sources and/or detectors can be removed and/or rearranged on the contact lens 102.

As seen in FIG. 4C, in an aspect, one or more light sources 404 can be located aside a detector 406 on the contact lens 102 within the hydrogel substrate of the contact lens and on or near an inner surface 420 of the contact lens that is adjacent to the eye when the contact lens is worn in the eye. According to this aspect, the light sources 404 can be configured to emit light 414 towards one or more blood vessels 418 located on the eye 104. In turn, the detectors 406 can be configured to detect light reflected 416 off of the one or more blood vessels. In an aspect, the one or more light sources can be located in a area that is not covered by an eyelid when the eye is open (e.g. on or around axis X of FIG. 4B). In an aspect, the one or more light sources can be located in a area that is covered by an eyelid when the eye is open (e.g. on or around axis Y of FIG. 4A).

With reference to FIG. 4D, presented is another cross-sectional view of an example contact lens 102 being worn in/on an eye 104. The contact lens 102 includes a contact lens circuit 106 and a pulse oximetry sensor consisting of multiple light sources 404 and detectors 406. One or more wires (not shown) can connect the contact lens circuit 106, light sources 404 and/or detectors 406. It should be appreciated that the multiple light sources and detectors of contact lens 102 are merely presented to demonstrate different configurations of light source and detector locations. In some aspects, one or more light sources and/or detectors can be removed and/or rearranged on the contact lens 102.

As seen in FIG. 4D, in an aspect, one or more light sources 404 can be located aside a detector 406 on the contact lens 102 within the hydrogel substrate of the contact lens and on or near an outer surface 422 of the contact lens that is opposite the inner surface and adjacent an eyelid 402 and/or 408 when the contact lens is worn in the eye. According to this aspect, the light sources 404 can be configured to emit light 414 towards one or more blood vessels 418 located in an eyelid 402 and/or 408. In turn, the detectors 406 can be configured to detect light reflected 416 off of the one or more blood vessels. In an aspect, the one or more light sources can be located in an area that is not covered by an eyelid when the eye is open (e.g. on or around axis X of FIG. 4B). According to this aspect, the one or more light sources 404 can be configured to emit light towards an eyelid when the wearer closes his or her eye. In another aspect, the one or more light sources 404 can be located in an area that is covered by an eyelid when the eye is open (e.g. on or around axis Y of FIG. 4A). According to this aspect, the one or more light sources 404 can be configured to emit light when towards an eyelid when the wearer closes his or her eye and/or opens his or her eye.

Continuing to FIG. 4E, presented is another cross-sectional view of an example contact lens 102 being worn in/on an eye 104. The contact lens 102 includes a contact lens circuit 106 and a pulse oximetry sensor consisting of at least one light source 404 and a detector 406. One or more wires (not shown) can connect the contact lens circuit 106, light source 404 and/or detector 406. The pulse oximeter presented in FIG. 4E is a transmittance pulse oximeter. In particular, as seen in FIG. 4E, the light source 404 and the detector 406 are located within the contact lens and on opposite sides of blood vessels through which light 424 is transmitted. In particular, the light source 404 can be located within the substrate at the perimeter edge of the contact lens and the detector 406 can be located directly across from the light source within the substrate at an opposite perimeter edge of the contact lens. Due to the curvature of the contact lens 102, the light source can be angled so that light 424 is emitted therefrom and passes through the eye 104 to be received at the detector 406 at the opposing side of the contact lens 102.

Figure 5B:
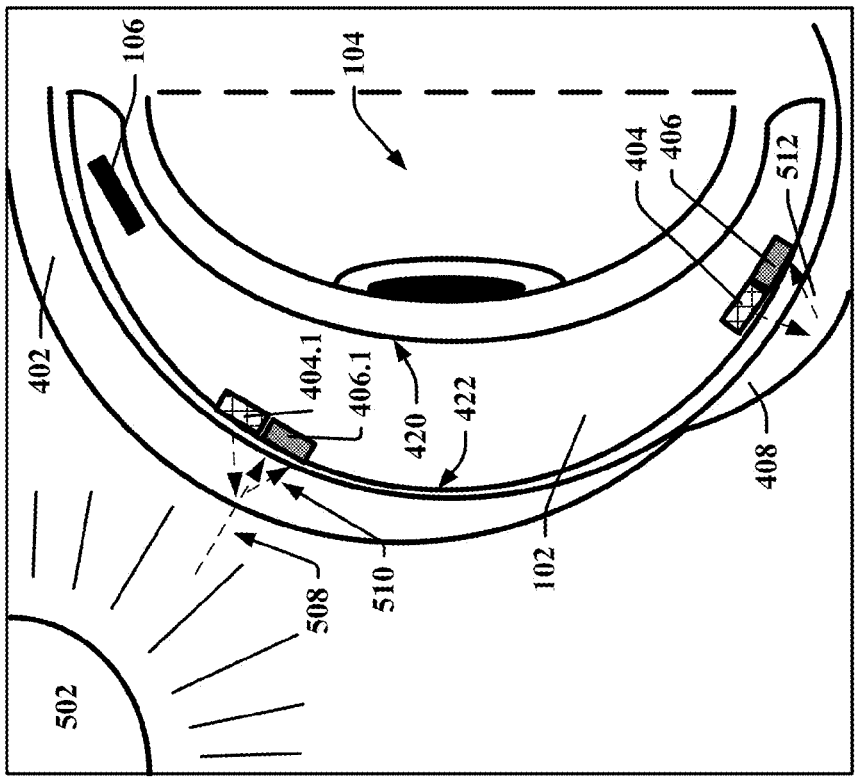
FIG. 5B depicts a cross-sectional view of an example contact lens being worn in/on an eye when the eye is closed in accordance with aspects described herein.
Figure 5A:
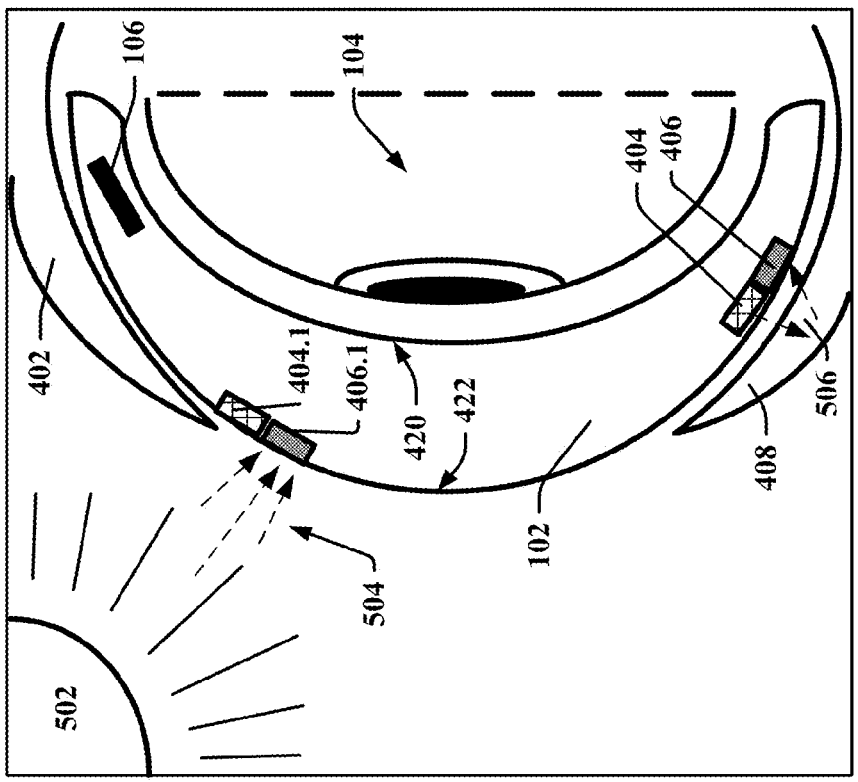
FIG. 5A depicts a cross-sectional view of an example contact lens being worn in/on an eye when the eye is open in accordance with aspects described herein.

Looking now to FIGS. 5A and 5B, presented are across-sectional views of an example contact lens 102 being worn in/on an eye 104. FIG. 5A depicts the contact lens under operation when the eye 104 is open and FIG. 5B depicts the contact lens under operation when the eye 104 is closed. FIGS. 5A and 5B demonstrate the detection capabilities of the contact lens pulse oximetry sensor regarding environmental light, particularly light from the sun 502.

With reference to FIG. 5A, the contact lens 102 includes a contact lens circuit 106 and a pulse oximetry sensor consisting of multiple light sources 404/404.1 and detectors 406/406.1. One or more wires (not shown) can connect the contact lens circuit 106, light sources 404 and/or detectors 406. It should be appreciated that the multiple light sources and detectors of contact lens 102 are merely presented to demonstrate different configurations of light source and detector locations. In some aspects, one or more light sources and/or detectors can be removed and/or rearranged on the contact lens 102.

As seen in FIG. 5A, in an aspect, a light source 404.1 can be located aside a detector 406.1 on the contact lens 102 within the hydrogel substrate of the contact lens and on or near an outer surface 422 of the contact lens. In an aspect, detector 406.1 can stand alone and does not need to be aside a light source 404.1. In other aspects, detector 406.1 can operate with light source 404.1 turned off and on. The detector 406.1 and light source 404.1 are further located within the hydrogel in an area of the contact lens 102 that is not covered by an eyelid 402/408 when the eye is open. According to this aspect, the detector is configured to receive direct environmental light 504 when the eye is open. In addition, as seen in FIG. 5B, the detector 406.1 is configured to received transmitted environmental light 508 when the eye 104 is closed. The transmitted environmental light 508 is light that is not absorbed by blood vessels in the eyelid 402 but transmitted there through such blood vessels with the sun 502 as the light source. In FIG. 5B, the eye is closed as indicated by the covering of the eye 104 by the upper eyelid 402.

In addition, in an aspect contact lens 102 as represented in FIGS. 5A and 5B can generate signals using light sources 404.1 and 404 under conditions when the eye 104 is opened and closed. Such additional signals can further be employed to calibrate the pulse oximetry sensor and/or to determine blood oxygenation levels and/or pulse rate.

With reference to FIG. 5A, contact lens 102 can also include light source 404 and detector 406 located on or near an outer surface 422 of the contact and within an area of the contact lens that is covered by an eyelid 408 when the eye is open. According to this aspect, light sources 404 can be configured to emit light towards one or more blood vessels located in eyelid 408 when the eye is open (FIG. 5A) and/or closed (FIG. 5B). In turn, detector 406 can be configured to detect light reflected off of the one or more blood vessels when the eye is open (reflected light 506 in FIG. 5A) and/or to detect light reflected off of the one or more blood vessels when the eye is closed (reflected light 512 in FIG. 5B). Further, light source 404.1 can be configured to emit light towards one or more blood vessels located in eyelid 402 when the eye is closed (FIG. 5B). In turn, detector 406.1 can be configured to detect light reflected off of the one or more blood vessels when the eye is closed (reflected light 510 in FIG. 5B).

Figure 6:
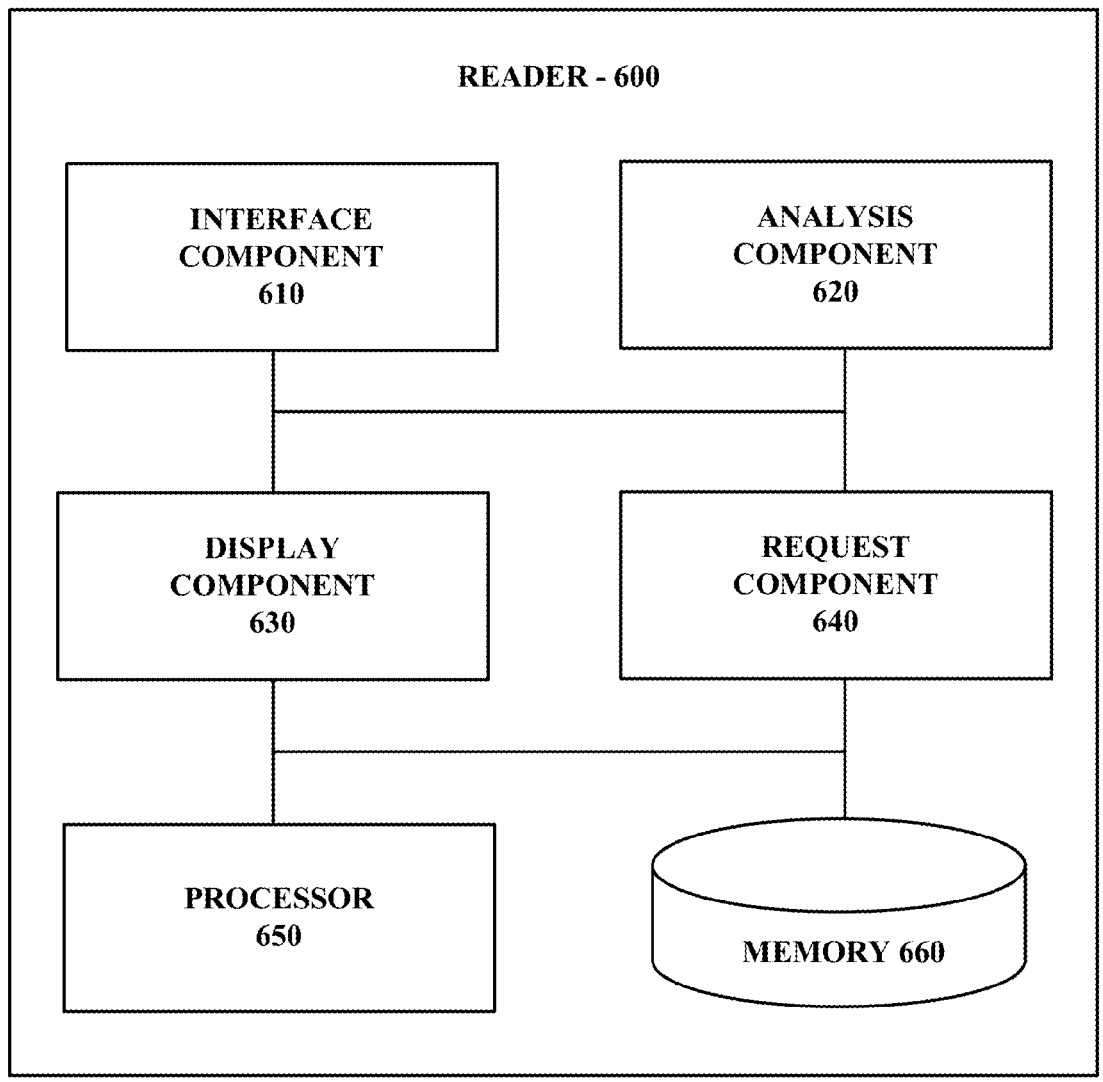
FIG. 6 is an illustration of an exemplary non-limiting reader device that receives from a contact lens, information indicative of blood oxygen content or pulse rate of a wearer of the contact lens in accordance with aspects described herein.

FIG. 6 is an illustration of an exemplary non-limiting reader device 600 that interfaces with a contact lens employing a pulse oximetry sensor to detect information indicative of a blood oxygen saturation level and/or a pulse rate of a wearer of the contact lens in accordance with aspects described herein. In various aspects, the reader device 600 can include one or more of the structure and/or functionality of the reader device 110 (and vice versa).

As shown in FIG. 6, reader device 600 can include interface component 610, analysis component 620, display component 630, and request component 640. In an embodiment, aspects of device 600 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Device 600 can include memory 660 for storing computer executable components and instructions. A processor 650 can facilitate operation of the computer executable components and instructions by device 600.

Interface component 610 interfaces with and receives from at least one contact lens, data relating to blood oxygen content and/or a pulse of a wearer of the contact lens. In particular, interface component 610 can interface with contact lenses described herein that comprise a contact lens circuit such as contact lens circuit 106 and/or contact lens circuit 200 (e.g. contact lens 102). In an aspect, interface component 610 employs a receiver, such as an RF receiver, to receive detected and/or determined information from a contact lens comprising a contact lens circuit as described herein. In some aspects, interface component 610 can receive from a contact lens, a determined value indicating blood oxygen content and/or pulse rate of a wearer of the contact lens. According to this aspect, the contact lens may include appropriate circuitry and components to process data detected by a pulse oximetry sensor thereon and/or therein.

In another aspect, the reader can receive raw data from a contact lens that is detected by a pulse oximetry sensor located thereon/therein. For example, the interface component 610 may request and receive calibration information and detected information indicative of the wearers blood oxygen level and/or pulse rate (e.g. a signal representative of an amount and wavelength of light received at the sensor's detector over time. According to this embodiment, the reader 600 can comprise an analysis component 620 that can analyze the received raw data and to determine a blood oxygen level and/or pulse rate of the wearer of the contact lens from which the data was transmitted. For example, the analysis component 620 can perform the same or similar analysis techniques as microprocessor 270 using processor 650 and memory 660. Further, memory 660 can store same or similar information as memory 260.

Request component 640 can transmit a request to a contact lens for data relating to a blood oxygen level and/or pulse rate of a wearer of the contact lens. For example, the request component 640 can request detected raw data and/or determined blood oxygen levels and/or pulse rates. In an aspect, the request can prompt the contact lens to perform specific types of detection and/or analysis. For example, the request may prompt the contact lens to generate and transmit data relating to a blood oxygen level and/or a pulse rate of a wearer of the contact lens, including calibration information. Such information can include information that is detected under specifically requested conditions. For example, the request component 640 can request data detected in response to opening and closing an eye in which the contact lens in worn. According to this aspect, the request component can instruct a wearer of the contact lens when and for how long to open and close his or her eye (e.g. via presenting a visual or audible signal to the wearer). As a result the reader device can control the collection of signals by the contact lens when the user opens and closes his or her eye.

For example, the request may include instructions for the pulse oximeter to undergo calibration. According to this aspect, the request can also signal the wearer of the contact lens to open and close his or her eye in accordance with procedure for generating calibration information. For instance, the request component 640 may send a calibration request to the contact lens and at the same time, instruct the wearer of the contact lens to hold his or her eye closed. In an aspect, the request component can signal an alarm, such as a sound or image, to indicate when the wearer of the contact lens should open and close his or her eye during the calibration process.

The reader device 600 can further include a display component 630 that presents a display or response corresponding to received and/or determined information. For example, the reader device may present digital display with a value of an individual's blood oxygen level and/or pulse rate. In another aspect, the reader device by employ speech software to audibly read out determined information. Reader device 600 can include any suitable computing device capable of wirelessly transmitting and receiving information, displaying information, sounding information, and/or processing data detected via a pulse oximeter provided on/or within a contact lens as described herein. For example, reader device 600 can include but is not limited to, a cellular phone, a smart phone, a personal digital assistant, an ipod, a watch, a wearable device, a tablet PC, a laptop computer, or a desktop computer.

Figure 7:
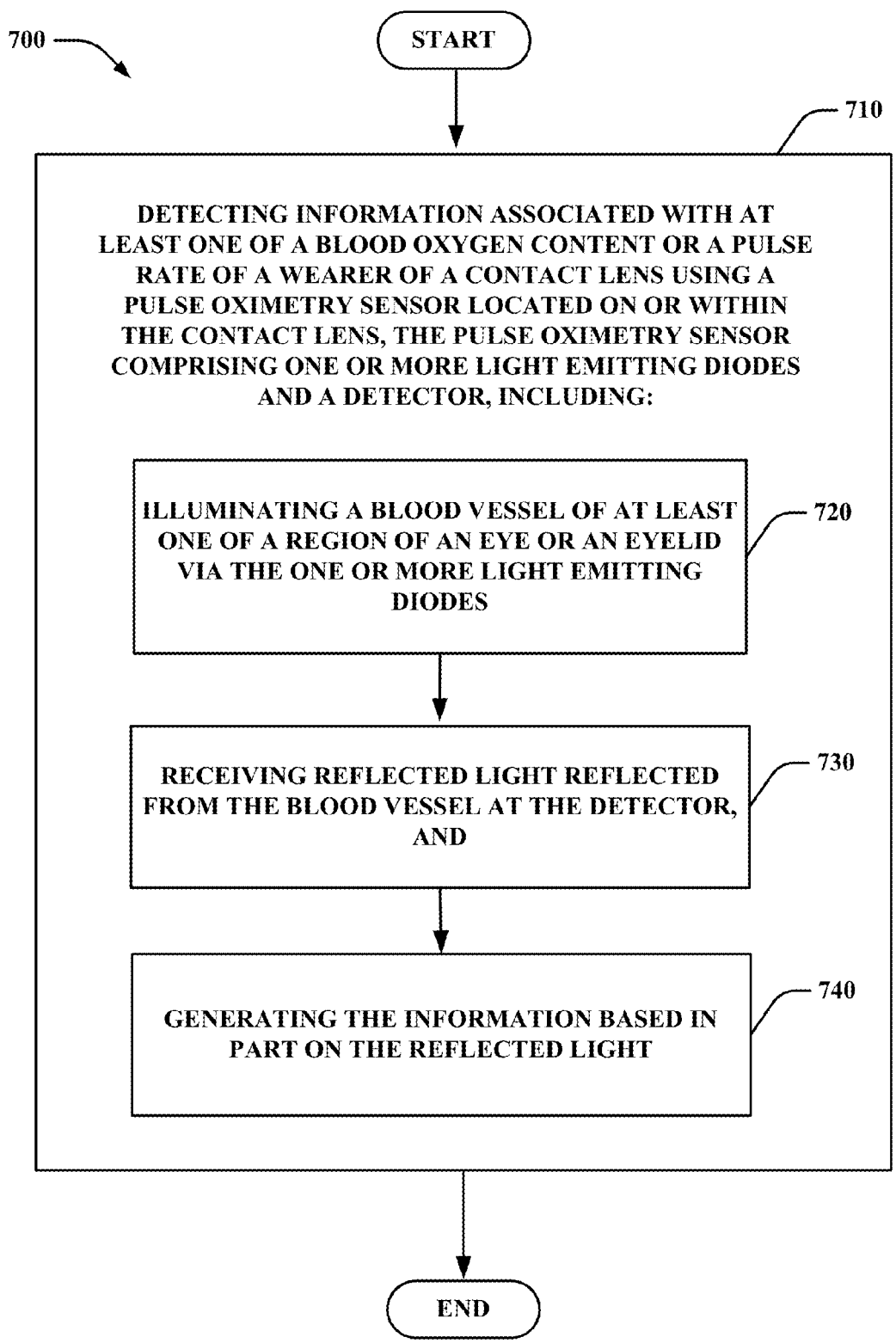
FIG. 7 is an exemplary flow diagram of a method for detecting information indicative of blood oxygen content or pulse rate of a wearer of a contact lens in accordance with aspects described herein.
Figure 8:
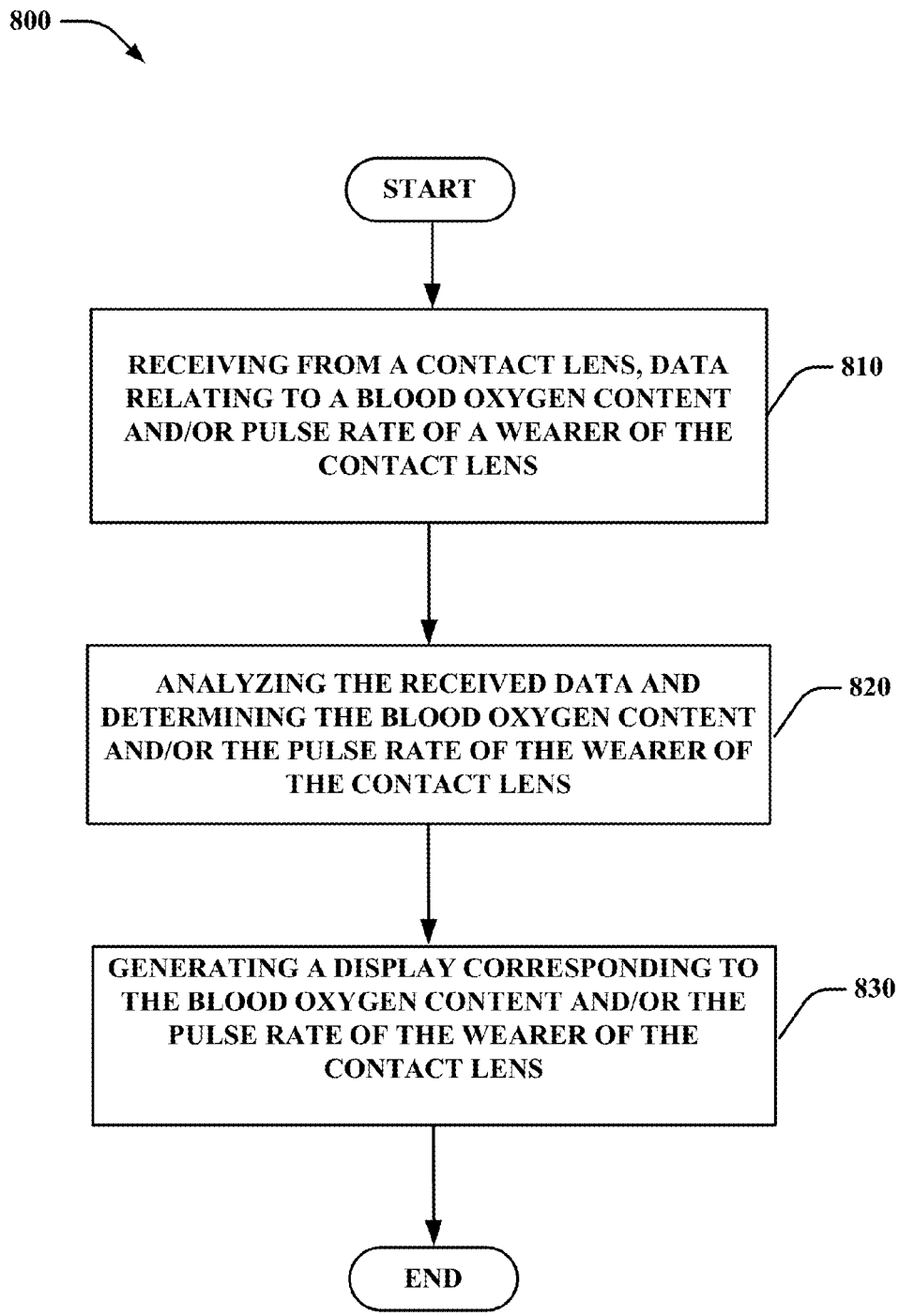
FIG. 8 is an exemplary flow diagram of a method that facilitates receiving from a contact lens, information indicative of blood oxygen content or pulse rate of a wearer of the contact lens using the contact lens in accordance with aspects described herein.

FIGS. 7-8 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 7, presented is a flow diagram of an example application of systems and apparatuses disclosed in this description in accordance with an embodiment. In an aspect, in exemplary methodology 700, a contact lens such as those described herein (e.g. 102 and the like) is employed to detect information pertaining to a blood oxygen content and/or pulse rate of a wearer of the contact lens. At 710, information associated with at least one of a blood oxygen content or a pulse rate of a wearer of a contact lens is detected using a pulse oximetry sensor located on or within the contact lens (e.g., pulse oximetry sensor 220 of contact lens 102). The pulse oximetry sensor comprises one or more light emitting diodes and a detector. The detecting includes illuminating a blood vessel of at least one of a region of an eye or an eyelid via the one or more light emitting diodes, 720, receiving light reflected from the blood vessel at the detector, 730, and generating the information based in part on the reflected light, 740 (e.g. using pulse oximetry sensor 220 of contact lens 102).

Turning now to FIG. 8, a method 800 can include receiving information detected by a contact lens relating to a blood oxygen content and/or pulse rate of a wearer of the contact lens (e.g. using reader device 110 or 600). At 810, data relating to a blood oxygen content and/or pulse rate of a wearer of the contact lens is received (e.g. using interface component 610). In an aspect, the data is received in response to a request for the data sent by a reader device at which the data is received. The request can initialize detection by the pulse oximetry sensor of the contact lens from which the data is generated and received from. At 820, the received data is analyzed and the blood oxygen content and/or pulse rate of a wearer of the contact lens determined (e.g. using analysis component 620). At 830, a display is generated corresponding to the blood oxygen content and/or pulse rate of a wearer of the contact lens (e.g. using display component 630).

Exemplary Networked and Distributed Environments

Figure 9:
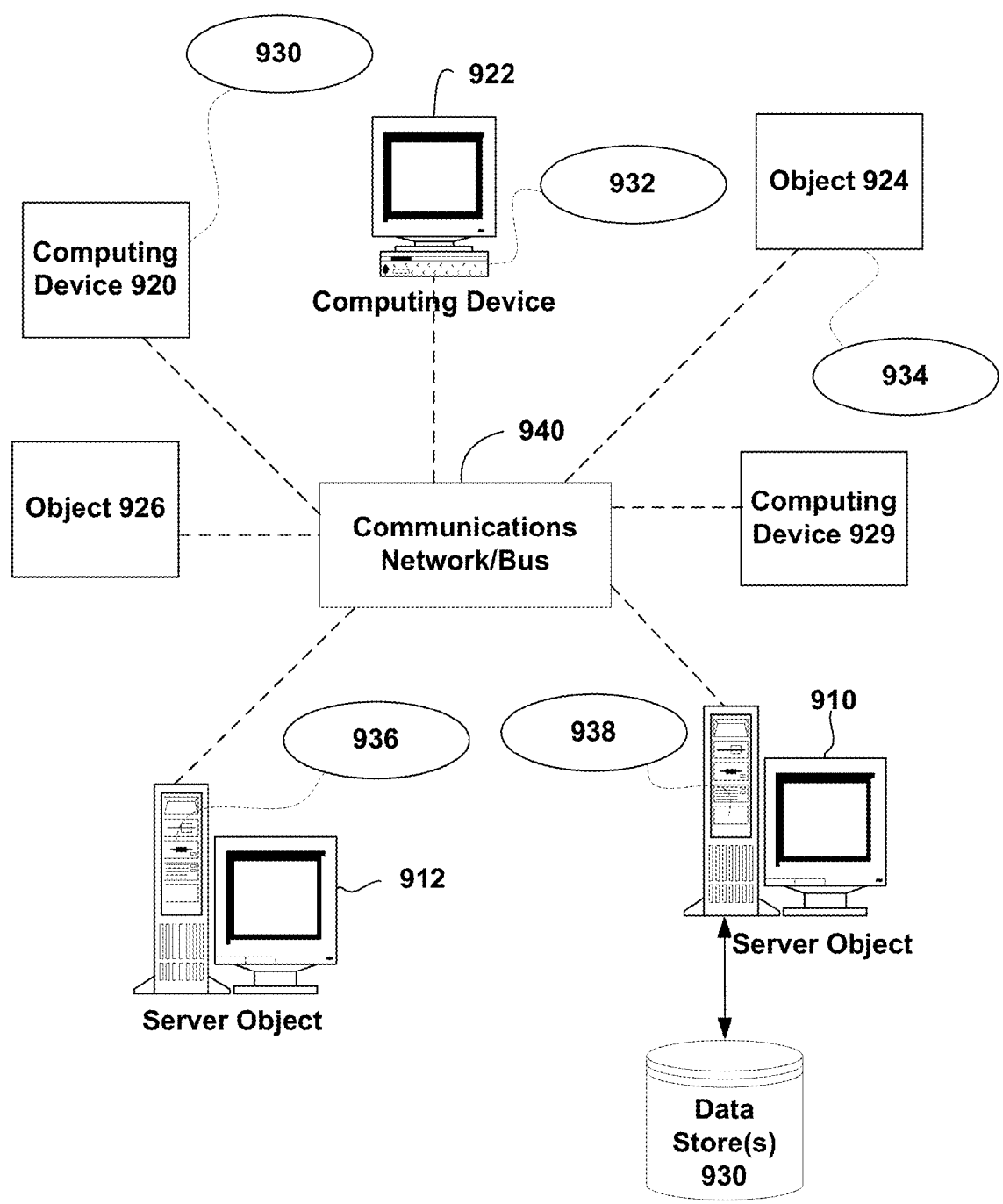
FIG. 9 is an illustration of a schematic diagram of an exemplary networked or distributed computing environment with which one or more aspects described herein can be associated.

FIG. 9 provides a schematic diagram of an exemplary networked or distributed computing environment with which one or more aspects described in this disclosure can be associated. The distributed computing environment includes computing objects 910, 912, etc. and computing objects or devices 920, 922, 924, 926, 928, etc., which can include programs, methods, data stores, programmable logic, etc., as represented by applications 930, 932, 934, 936, 938. It can be appreciated that computing objects 910, 912, etc. and computing objects or devices 920, 922, 924, 926, 928, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 910, 912, etc. and computing objects or devices 920, 922, 924, 926, 928, etc. can communicate with one or more other computing objects 910, 912, etc. and computing objects or devices 920, 922, 924, 926, 928, etc. by way of the communications network 940, either directly or indirectly. Even though illustrated as a single element in FIG. 9, network 940 can include other computing objects and computing devices that provide services to the system of FIG. 9, and/or can represent multiple interconnected networks, which are not shown.

In a network environment in which the communications network/bus 940 can be the Internet, the computing objects 910, 912, etc. can be Web servers, file servers, media servers, etc. with which the client computing objects or devices 920, 922, 924, 926, 928, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the reader device described herein. In various aspects, the data store can be any repository for storing information transmitted to or received from the contact lens.

Figure 10:
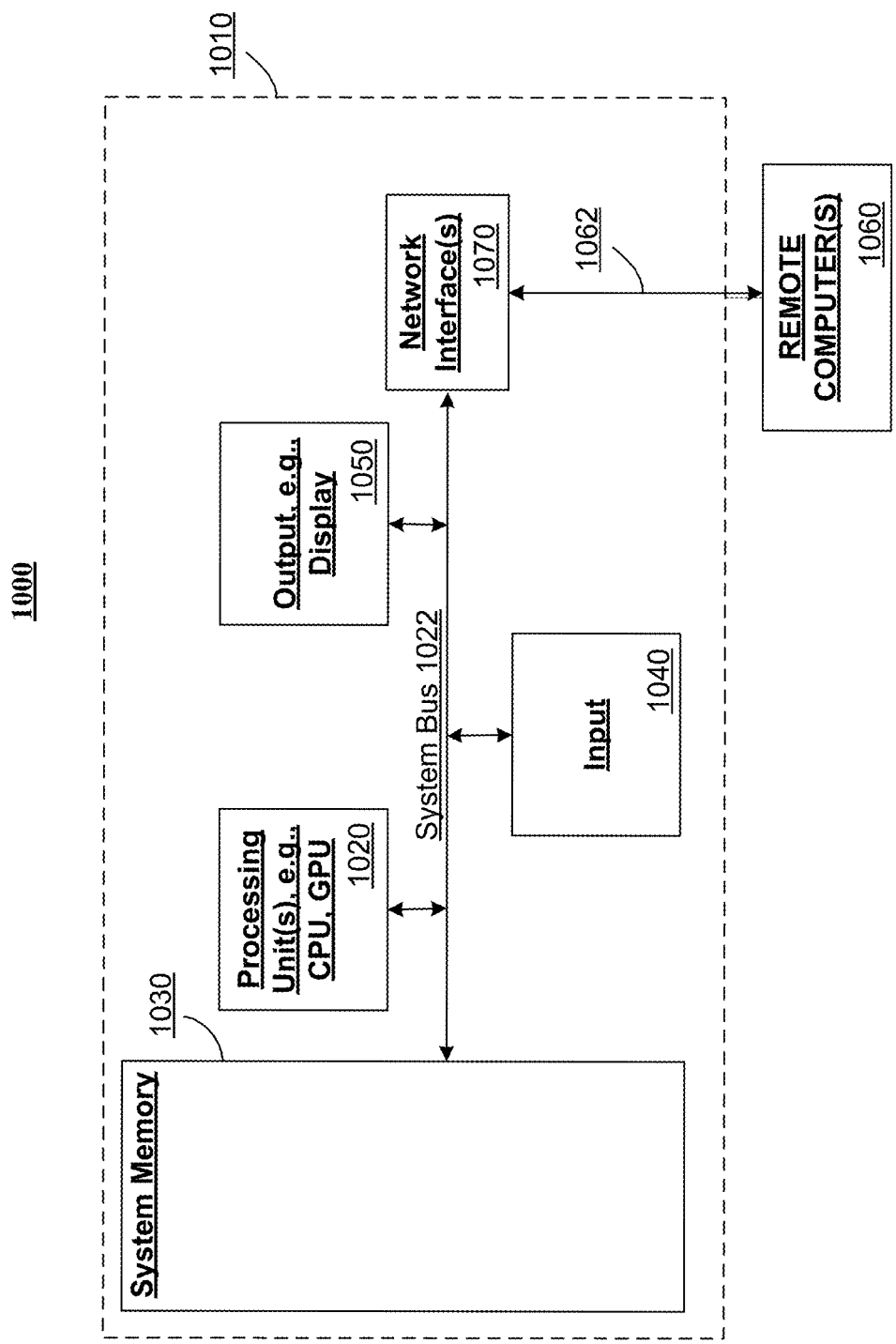
FIG. 10 is an illustration of a schematic diagram of an exemplary computing environment with which one or more aspects described herein can be associated.

FIG. 10 illustrates an example of a suitable computing system environment 1000 in which one or aspects of the aspects described in this disclosure can be implemented. Components of computer 1010 can include, but are not limited to, a processing unit 1020, a system memory 1030, and a system bus 1022 that couples various system components including the system memory to the processing unit 1020.

Computer 1010 typically includes a variety of computer readable media and can be any available media that can be accessed by computer 1010. The system memory 1030 can include computer storage media in the form of volatile and/or nonvolatile memory such as read only memory (ROM) and/or random access memory (RAM). By way of example, and not limitation, memory 1030 can also include an operating system, application programs, other program components, and program data.

A user can enter commands and information into the computer 1010 through input devices 1040 (e.g., keyboard, keypad, a pointing device, a mouse, stylus, touchpad, touch screen, motion detector, camera, microphone or any other device that allows the user to interact with the computer 1010). A monitor or other type of display device can be also connected to the system bus 1022 via an interface, such as output interface 1050. In addition to a monitor, computers can also include other peripheral output devices such as speakers and a printer, which can be connected through output interface 1050.

The computer 1010 can operate in a networked or distributed environment using logical connections to one or more other remote computers, such as remote computer 1060. The remote computer 1060 can be a personal computer, a server, a router, a network PC, a peer device or other common network node, or any other remote media consumption or transmission device, and can include any or all of the elements described above relative to the computer 1010. The logical connections depicted in FIG. 10 include a network 1070, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
   a substrate that forms at least part of a body of the contact lens; and
   a pulse oximetry sensor located on or within the substrate configured to detect information associated with at least one of a blood oxygen content or a pulse rate of a wearer of the contact lens, the pulse oximetry sensor comprising:
      one or more light emitting diodes configured to illuminate a blood vessel of a region of an eyelid; and
      a detector configured to receive light reflected from the blood vessel of the eyelid, receive environmental light transmitted through the blood vessel of the eyelid, and generate the information based, at least in part, on the reflected light and the transmitted light;
   the contact lens configured to maintain an orientation when worn on an eye, such that the one or more light emitting diodes and the detector are covered by the eyelid when the eye is open.

2. The contact lens of claim 1, wherein the information includes a signal indicating an amount of light reflected from the blood vessel in response to illumination of the blood vessel by the one or more light emitting diodes.

3. The contact lens of claim 1, wherein the one or more light emitting diodes are configured to illuminate the blood vessel over a period of time as the blood vessel expands and contracts, and wherein the information includes a signal indicating time variance in an amount of light received from the blood vessel, in response to illumination of the blood vessel by the one or more light emitting diodes, between blood vessel expansion and contraction.

4. The contact lens of claim 1, wherein the information includes a signal indicating an amount of light transmitted through the blood vessel of the eyelid.

5. The contact lens of claim 1, wherein at least one of the one or more light emitting diodes are configured to emit infrared light.

6. The contact lens of claim 1, wherein the one or more light emitting diodes include a first diode that is configured to emit infrared light and a second diode that is configured to emit red light.

7. The contact lens of claim 1, further comprising:
   a circuit disposed on or within the substrate configured to receive the information associated with the at least one of the blood oxygen content or the pulse rate; and
   a transceiver configured to transmit the information.

8. The contact lens of claim 7, wherein the pulse oximetry sensor is configured to detect the information in response to a request from a device external to the contact lens and wherein the transceiver is configured to receive the request and transmit the information in response to the request.

9. The contact lens of claim 8, wherein the transceiver is configured to transmit a message indicating at least one of the blood oxygen content or the pulse rate of the wearer of the contact lens in response to a determination that the blood oxygen content or the pulse rate is outside a predetermined range.

10. The contact lens of claim 7, further comprising a processor configured to determine at least one of the blood oxygen content or the pulse rate of the wearer of the contact lens based on the information.

11. A method comprising:
   detecting, with one or more detectors of a pulse oximetry sensor, light reflected from a blood vessel of a region of an eyelid and environmental light transmitted through the blood vessel of the eyelid, wherein the pulse oximetry sensor is located on or within a contact lens; and
   generating information associated with at least one of a blood oxygen content or a pulse rate of a wearer of the contact lens based, at least in part, on the reflected light and the transmitted light and wherein the contact lens is configured to maintain an orientation when worn on an eye such that the one or more detectors are covered by the eyelid when the eye is open.

12. The method of claim 11, wherein the detecting the information comprises:
illuminating the blood vessel with one or more light emitting diodes of the pulse oximetry sensor.

13. The method of claim 12, wherein the information includes a signal indicating an amount of light reflected from the blood vessel in response to the illuminating.

14. The method of claim 12, wherein the illuminating further comprises, via the one or more light emitting diodes, illuminating the blood vessel over a period of time as the blood vessel expands and contracts, and wherein the information includes a includes a signal indicating a time variance in an amount of light reflected from the blood vessel, in response to the illuminating, between blood vessel expansion and contraction.

15. The method of claim 12, wherein at least one of the one or more light emitting diodes emit infrared light.

16. The method of claim 12, wherein the one or more light emitting diodes include a first diode that emits infrared light and a second diode that emits red light.

17. The method of claim 11, further comprising transmitting the information to a device external to the contact lens.

18. The method of claim 11, further comprising:
receiving a request for the information from a device external to the contact lens, wherein the detecting the information comprises detecting the information in response to the request; and
transmitting the information to the device in response to the request.

19. A device, comprising:
a memory that stores computer executable components; and
a processor that executes the following computer executable components stored in the memory:
an interface component that interfaces with and receives from a contact lens, data relating to at least one of a blood oxygen content or a pulse rate of a wearer of a contact lens;
an analysis component that analyzes the received data and determines at least one of the blood oxygen content or the pulse rate of a wearer of a contact lens;
a display component that generates a display corresponding to the data;
a request component that transmits a request to the contact lens, wherein the request prompts the contact lens to generate and transmit data relating to at least one of a blood oxygen content or a pulse rate of a wearer of a contact lens, and wherein the request prompts the contact lens to generate data when an eye on which the contact lens is worn is open and when the eye on which the contact lens is worn is closed.

* * * * *